United States Patent
Donitzky et al.

(10) Patent No.: US 9,974,691 B2
(45) Date of Patent: May 22, 2018

(54) DEVICE AND PROCESS FOR SURGERY ON THE HUMAN EYE

(75) Inventors: Christof Donitzky, Eschenau/Eckental (DE); Klaus Vogler, Eschenau/Eckental (DE)

(73) Assignee: WaveLight GmbH, Erlangen (DE)

( * ) Notice: Subject to any disclaimer, the term of this patent is extended or adjusted under 35 U.S.C. 154(b) by 579 days.

(21) Appl. No.: 14/345,378

(22) PCT Filed: Oct. 10, 2011

(86) PCT No.: PCT/EP2011/005061
§ 371 (c)(1),
(2), (4) Date: Mar. 24, 2014

(87) PCT Pub. No.: WO2013/053366
PCT Pub. Date: Apr. 18, 2013

(65) Prior Publication Data
US 2014/0364840 A1    Dec. 11, 2014

(51) Int. Cl.
*A61B 18/20*    (2006.01)
*A61F 9/008*    (2006.01)

(52) U.S. Cl.
CPC .......... *A61F 9/008* (2013.01); *A61F 9/00827* (2013.01); *A61F 2009/00872* (2013.01); *A61F 2009/00897* (2013.01)

(58) Field of Classification Search
CPC .. A61F 9/008; A61F 9/00802; A61F 9/00804; A61F 9/00825; A61F 9/00827; A61F 2009/00872; A61F 2009/00897; A61B 18/20; A61B 2018/20351; A61B 2018/20353; A61B 2018/20355

USPC ............................................. 606/4–6, 10–12
See application file for complete search history.

(56) References Cited

U.S. PATENT DOCUMENTS

| 5,782,822 A | 7/1998 | Telfair et al. |
| 5,993,438 A | 11/1999 | Juhasz et al. |
| 6,110,166 A | 8/2000 | Juhasz |
| 7,351,241 B2 * | 4/2008 | Bendett ............... A61F 9/00827 128/898 |

(Continued)

FOREIGN PATENT DOCUMENTS

| EP | 0770370 A2 | 5/1997 |
| JP | 09122168 H | 5/1997 |

(Continued)

*Primary Examiner* — Ahmed Farah

(57) ABSTRACT

A laser apparatus is controlled by a control program that operates to use laser radiation to generate an incision figure in the cornea of an eye, the incision figure including an incision that bounds a corneal tissue volume. The control program operates to move the radiation focus in a radiation propagation direction successively in a plurality of superposed planes such that the radiation focus is moved without motion control in the propagation direction. The control program provides, for each plane, for a meandering scan path of the radiation focus that extends outside the tissue volume. The control program operates to allow through to the eye, in each plane, at least such radiation pulses that generate the first incision and to blank, in at least a fraction of the planes, at least a fraction of radiation pulses assigned to regions of the path that are at a distance from the incision.

8 Claims, 7 Drawing Sheets

(56) References Cited

U.S. PATENT DOCUMENTS

| | | | |
|---|---|---|---|
| 8,092,446 B2* | 1/2012 | Bischoff | A61F 9/00827 128/898 |
| 8,246,610 B2 | 8/2012 | Riedel et al. | |
| 8,449,534 B2* | 5/2013 | Donitzky | A61F 9/00804 606/5 |
| 8,491,577 B2* | 7/2013 | Kittelmann | A61F 9/008 606/5 |
| 9,370,445 B2* | 6/2016 | Wiechmann | A61F 9/008 |
| 2005/0197655 A1* | 9/2005 | Telfair | A61B 18/20 606/5 |
| 2006/0195076 A1 | 8/2006 | Blumenkranz et al. | |
| 2007/0293851 A1 | 12/2007 | Muhlhoff | |
| 2008/0039825 A1 | 2/2008 | Lai | |
| 2008/0077121 A1 | 3/2008 | Rathjen | |
| 2009/0171329 A1 | 7/2009 | Raksi | |
| 2009/0299347 A1 | 12/2009 | Vogler et al. | |
| 2010/0076418 A1 | 3/2010 | Rathjen | |
| 2010/0305553 A1* | 12/2010 | Kittelmann | A61F 9/008 606/4 |
| 2012/0083775 A1* | 4/2012 | Donitzky | A61F 9/00804 606/5 |
| 2012/0239014 A1 | 9/2012 | Rathjen et al. | |
| 2013/0281992 A1* | 10/2013 | Seiler | A61F 9/00827 606/5 |

FOREIGN PATENT DOCUMENTS

| | | |
|---|---|---|
| JP | 11-192253 | 7/1999 |
| JP | 2006341103 A2 | 12/2006 |
| JP | 2008-526384 | 7/2008 |
| RU | 2009114667 A | 10/2010 |
| RU | 2011102846 A | 8/2012 |
| WO | 2008014419 A2 | 1/2008 |
| WO | 2010000278 A1 | 1/2010 |
| WO | 20100136050 | 12/2010 |

* cited by examiner

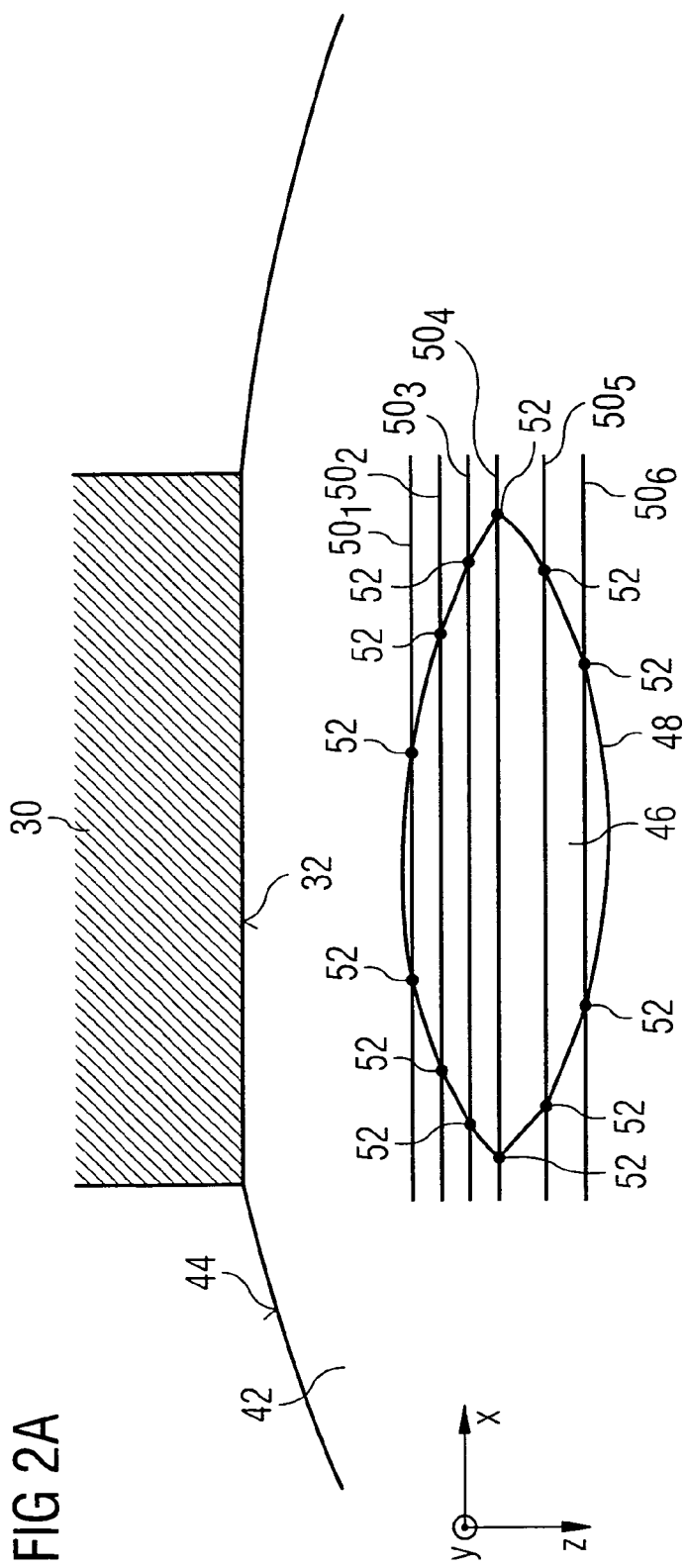

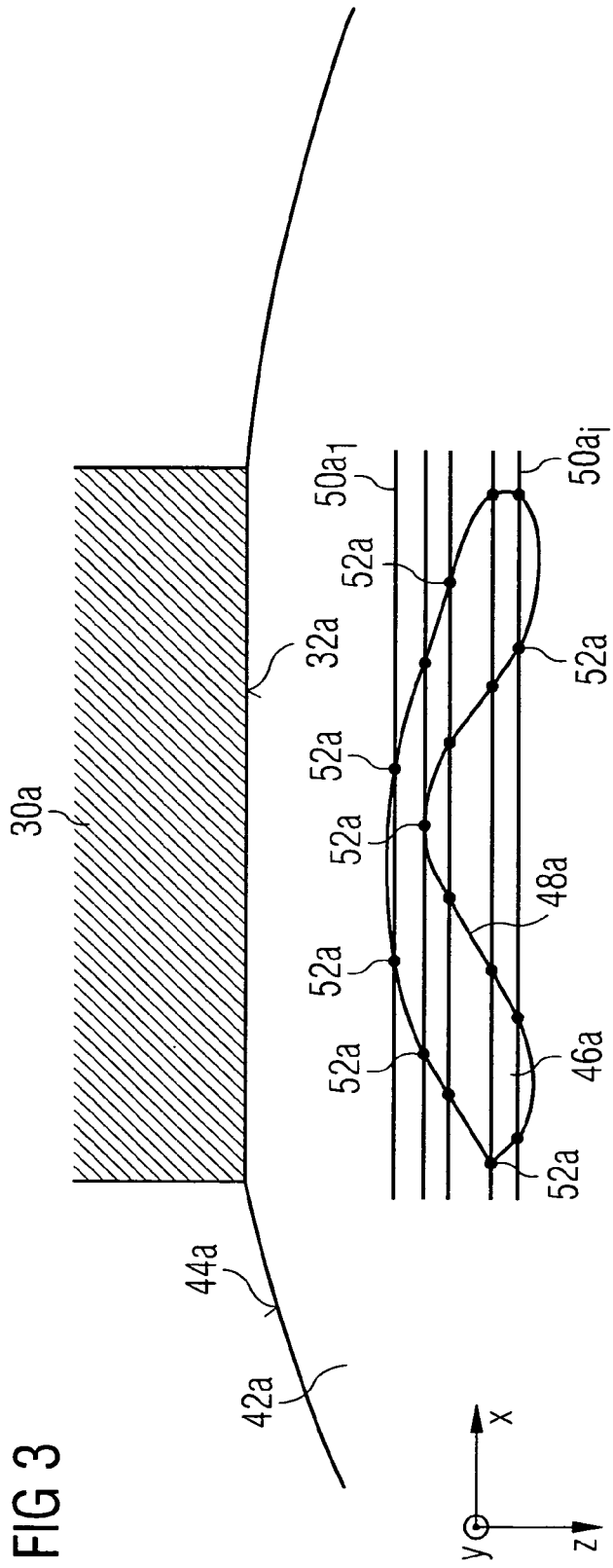

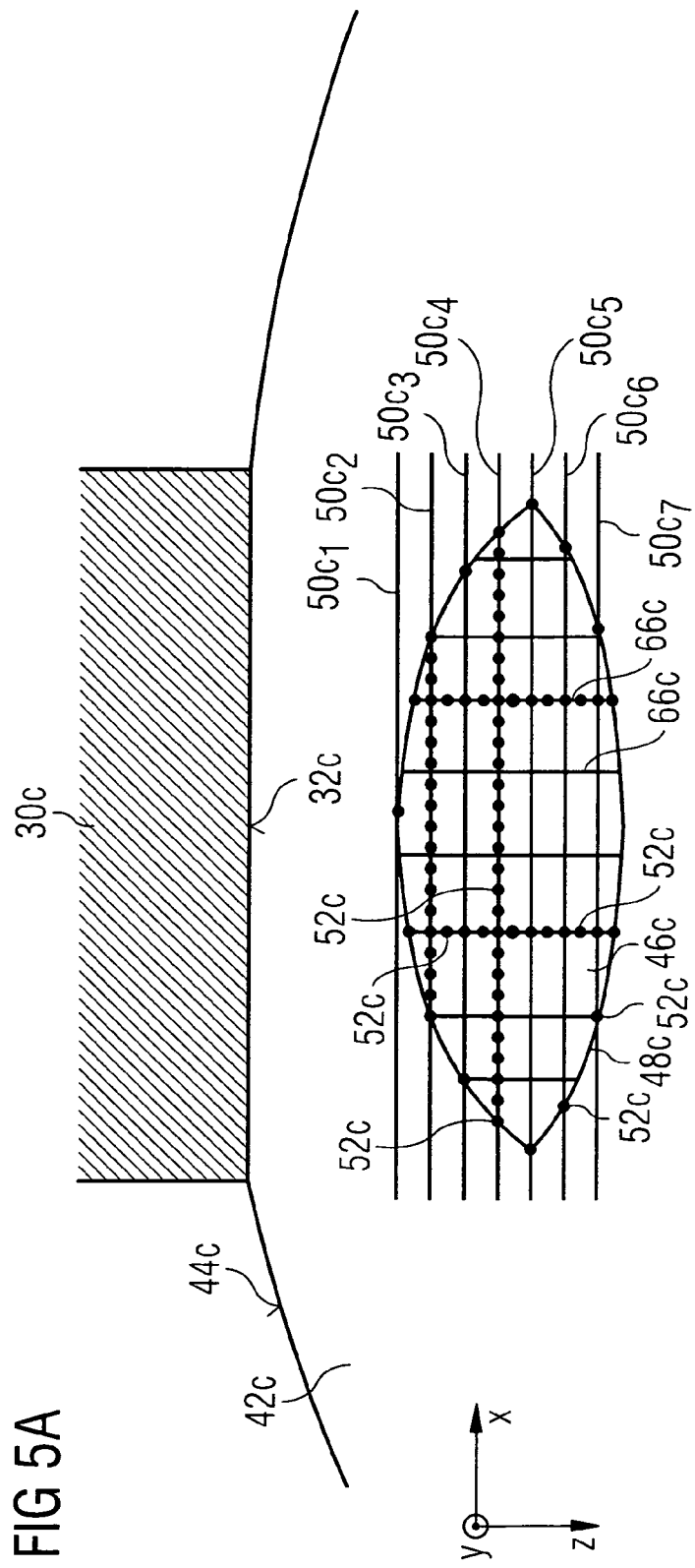

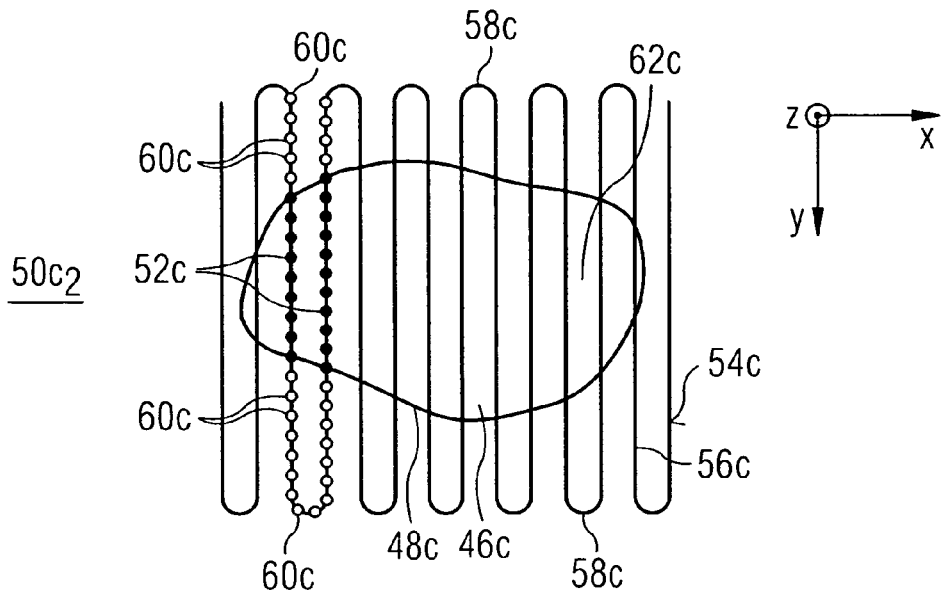
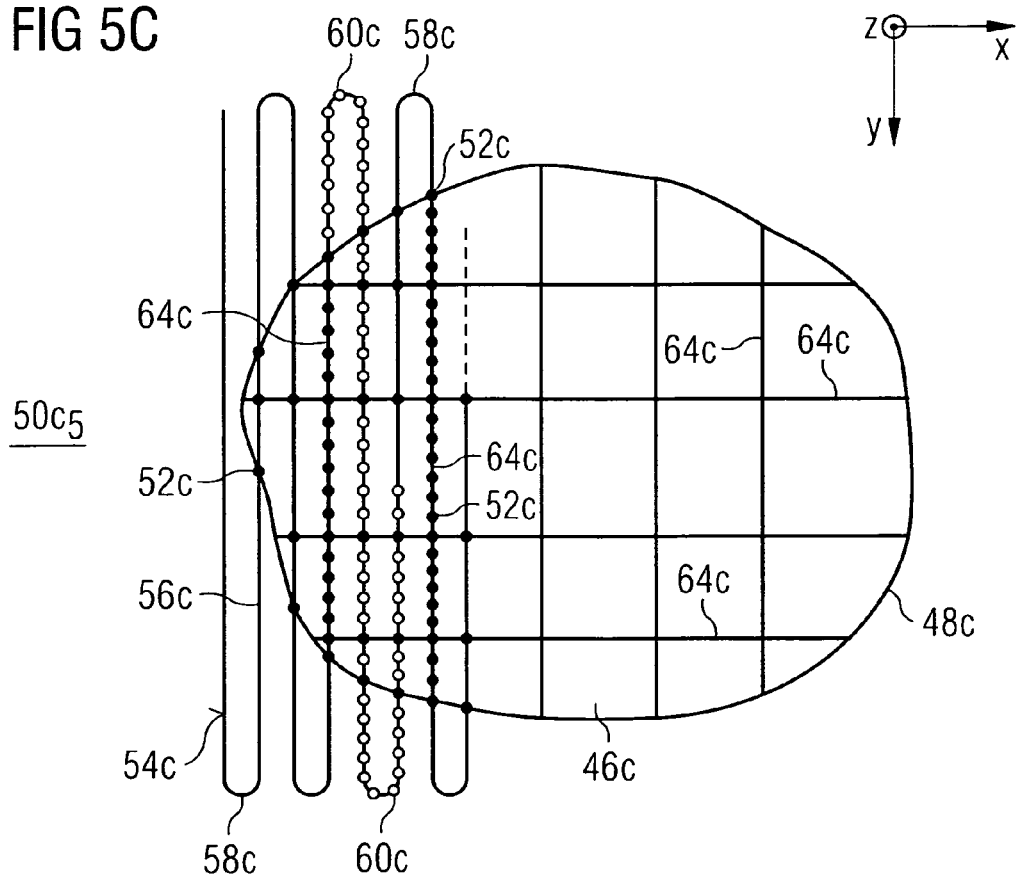

DEVICE AND PROCESS FOR SURGERY ON THE HUMAN EYE

CROSS REFERENCE TO RELATED APPLICATIONS

This application is a section 371 national stage phase of International Application No. PCT/EP2011/005061, filed 10 Oct. 2011, titled "DEVICE AND PROCESS FOR SURGERY ON THE HUMAN EYE," which is hereby incorporated by reference in its entirety.

TECHNICAL FIELD

The invention is concerned with laser-surgical treatment of the human eye and in particular with the generation of a three-dimensional incision figure in the corneal stroma.

BACKGROUND

The use of focused pulsed laser radiation for the purpose of generating incisions in the corneal tissue or in other tissue parts of the human eye has been the subject of intense research in human ophthalmology for some time. Instruments are also already on the market that provide a function of incision generation with laser radiation of such a type. Ordinarily in this connection, ultra-short-pulse laser radiation with pulse durations within e.g. the femtosecond range finds application. However, the invention is not restricted to this; to the extent that generation of an incision in corneal eye tissue is possible also with shorter or longer pulse durations, these are likewise to be encompassed by the invention; for example, pulse durations within the attosecond range or within the one-digit, two-digit or three-digit picosecond range.

A physical effect that is utilised in the course of the generation of an incision by means of pulsed laser radiation is the so-called laser-induced optical breakthrough, which results in a so-called photodisruption, the magnitude of which is limited roughly to the extent of the radiation focus at the waist point of the radiation. As a result of juxtaposing a plurality of such photodisruptions, diverse and comparatively complex incision figures can be generated in the eye tissue.

An exemplary application of the generation of an incision by means of pulsed laser radiation is so-called LASIK (laser in-situ keratomileusis). In this surgical procedure—which is generally to be classified as refractive surgery, that is to say, surgery aimed at the elimination or at least improvement of defective imaging properties of the eye—firstly the human cornea is cut open horizontally (from the point of view of the reclining patient), whereby a small cover (ordinarily called a flap in specialist circles) arises which can be folded aside. After the flap has been folded aside, in the stroma of the cornea that has been exposed in this way a so-called ablation is effected by means of laser radiation (for example, excimer radiation with a wavelength of 193 nm), i.e. stromal tissue is removed in accordance with a suitable ablation profile computed beforehand for the patient. After this the small cover is folded back, the healing process proceeding comparatively painlessly and quickly. After this intervention the cornea has different imaging properties, in which connection a very largely total elimination of the prior defective vision is achieved in the best case.

In the prior 'classical' procedure the cutting of the flap is effected with a mechanical microkeratome, in which connection, however, cutting the flap using laser technology has also recently been contemplated. The existing conceptions for this frequently provide for an applanation (levelling) of the anterior surface of the cornea by abutment against a planar abutment surface of a contact element that is transparent to the laser radiation, the flap then being generated by a bed incision situated at constant depth and by a lateral incision extending from the bed incision as far as the surface of the cornea. The levelling of the cornea permits the bed incision to be executed as a two-dimensional incision, for which solely a control of the location of the radiation focus in a plane perpendicular to the direction of propagation of the radiation (designated in conventional notation as the x-y plane) is required, without undertaking a control of the location of the radiation focus in the direction of propagation of the laser radiation (this direction is designated, according to conventional notation, as the z-direction). For the generation of the bed incision, the radiation focus is moved, for example, along a meandering scan path, i.e. a tortuous path that is composed of a plurality of rectilinear path portions situated next to one another in parallel which are connected to one another at their ends by means of redirecting-portions which are curved in arcuate manner or angular. For the generation of the lateral incision, the radiation focus is moved, for example, along a helical or spiral path ascending from the bed incision to the surface of the cornea, or along several superposed circular paths. Since at invariable pulse repetition rate the spacing of consecutive radiation pulses in the reversing-portions of the meandering scan path of the bed incision may decrease, in PCT/EP 2009/003730 a selective blanking is proposed of radiation pulses that are situated in regions of the meandering scan path that lie outside the lateral incision. By this means, thermal damage in the reversing-portions of the meandering scan path is intended to be avoided.

Another form of operation in which incisions are generated in the cornea by means of pulsed laser radiation is laser-assisted corneal lenticle extraction. In this case, in the stroma of the cornea a tissue volume—which, for example, has the shape of a small disc—is cut free which can then be extracted from the eye through an auxiliary incision. Depending on the indication (e.g. myopia, hyperopia), the lenticle to be removed may have varying shape. For the purpose of cutting the lenticle free, the procedure hitherto has frequently been such that firstly a lower incision bounding the underside of the lenticle (posterior side of the lenticle) and subsequently an upper incision bounding the upper side of the lenticle (anterior side of the lenticle) are generated in the cornea, both incisions frequently being three-dimensional and each requiring a z-control of the radiation focus. For both incisions the radiation focus is moved, for example along a meandering scan path, whereby at each point of the meandering scan path the z-position of the radiation focus is set to the position of the incision in question. During the scanning of the meandering scan path it may accordingly be necessary, time and time again, to adjust the radiation focus in the z-direction, in which connection under certain circumstances this may be necessary continuously from radiation pulse to radiation pulse.

A similar procedure can frequently also be noted in the case of the generation, using laser technology, of corneal keratoplasty incisions, i.e. incisions by which a piece of corneal tissue that is diseased or injured, and therefore to be transplanted, or a piece of corneal tissue of a donor eye serving as donor material is cut free. To be mentioned especially in this connection are endothelial and epithelial keratoplasty incisions. In the case of corneal keratoplasties, the requisite keratoplasty incisions may occasionally be considerably complex. This gives rise to comparatively frequent z-adjustments of the radiation focus if an attempt is being made to generate a three-dimensional incision with a single meandering scan path.

With a view to x-y adjustment of the radiation focus, sufficiently fast scanners are available which, for example, operate with galvanometrically controlled scanner mirrors. On the other hand, available z-scanners—that is to say, scanners that enable a focus displacement in the z-direction—are frequently slow in comparison with galvanometric mirror scanners. Depending on the complexity of the shape of the incision to be generated, i.e. depending on the extent of the z-focus displacements to be executed when sweeping the surface defining the incision, the requisite period of time for the generation of the incision, and consequently the entire duration of the operation, may therefore be undesirably long.

BRIEF SUMMARY

Against this background, an object of the invention is to demonstrate a method by which, in the case of the generation of an incision in corneal eye tissue using laser technology, even comparatively complex three-dimensional incision figures can be generated in an acceptably short time.

With a view to achieving this object, according to one aspect in accordance with the invention a device is provided for surgery on the human eye, including a laser apparatus for making available pulsed focused laser radiation, the laser apparatus being controlled by a control program in such a manner that by means of the laser radiation it is capable of generating an incision figure in the cornea of an eye to be treated, and the incision figure including a first incision that bounds a corneal tissue volume to be removed. The generation of the first incision in this case requires a motion control of the radiation focus in the direction of propagation of the radiation. The control program is designed in such a manner that for the generation of the incision figure the radiation focus is moved successively in a plurality of superposed planes in which a movement of the radiation focus is possible in each instance without motion control in the direction of propagation of the radiation (z-direction). For each plane the control program provides, for example, for a meandering scan path of the radiation focus that, at least in the region of its reversing-points, extends outside the tissue volume. The control program is designed to allow through to the eye, in each plane, at least such radiation pulses which serve for generating the first incision. Furthermore, the control program is designed to blank, in at least a fraction of the planes, in each instance at least a fraction (i.e. a partial number) of those radiation pulses which are assigned to regions of the meandering scan path that are situated at a distance from the first incision.

The invention is based on the idea of providing, for the purpose of generating a three-dimensional corneal incision figure, several superposed scan planes (incision planes) in which the radiation focus is moved in each instance along a predetermined scan path that is independent of the concrete shape of the incision, whereby radiation pulses are allowed through wherever a photodisruption is to be generated in the plane in question—that is to say, above all where the incision to be generated intersects the plane. At the same time, the device according to the invention has a controllable blanking unit which makes it possible to blank individual radiation pulses selectively, so that they do not reach the eye. The blanking unit, which may also be designated as an optical switch, may include, for example, an electro-optical or acousto-optical modulator or a Pockels cell. Through provision of a blanking mechanism of such a type, in each plane radiation pulses can be blanked where no photodisruption is intended—that is to say, for example, outside the regions in which the incision to be generated in the volume and the plane in question, for example a horizontal plane, intersect.

For each plane the same path pattern of the scan path may have been predetermined, in which connection a meandering scan path was mentioned above. It should be pointed out that the invention is not, in principle, limited to meandering scan paths; instead of this, other types of scan paths are also conceivable with which points that in themselves are arbitrary in the plane in question can be approached, so that, when required, a large-area continuous incision can be generated in a plane. Conceivable as an alternative to a meandering scan path is, for example, a spiral scan pattern. The pattern of the scan path is preferentially the same for all planes.

In each plane the predetermined scan path can be scanned without z-control of the radiation focus. If the scan path of a plane is only fully swept before the radiation focus is moved into another plane, it is possible to keep the z-displacements of the radiation focus that are needed for the generation of an incision small, and thereby to keep the time delay due to such z-focus displacements within acceptable limits. It has been shown that the speed advantage of conventional galvanometric x-y scanners can readily compensate for the increased x-y scan effort of the invention, so that shorter treatment-times can be expected overall. The concept, according to the invention, of the splitting of the generation of an incision onto several planes is, in addition, applicable to incision geometries that in themselves are arbitrary.

According to one configuration, the control program may be configured to allow through to the eye in at least a fraction of the planes, if desired in each plane, in each instance only such radiation pulses which serve for generating the first incision. The first incision is, as defined above, such an element of the incision figure which defines the enveloping contour of the corneal tissue volume to be removed. The aforementioned configuration then guarantees that, at least in a fraction of the planes, photodisruptions are generated only where the first incision intersects the plane in question. This concept can be applied to all planes, so that the incision figure as a whole then includes only the first incision, and in each plane photodisruptions are generated only at the lines of intersection between the surface of the first incision and the plane in question. In this way, the entire tissue volume to be removed can be cut out as a single, continuous piece of tissue.

In an alternative configuration it is, however, conceivable to segment the tissue volume to be removed—i.e. to subdivide it into several (at least two), in each instance separately extractable, partial volumes. For this purpose the incision figure may include at least one further incision that subdivides the tissue volume bounded by the first incision into partial volumes that are separate from one another. The control program in this case is designed to allow through to the eye, in the planes, at least such radiation pulses which serve for generating the at least one further incision.

By such segmentation of the tissue volume to be removed as a whole into partial volumes the removal of tissue can be simplified, since smaller volume fractions can be extracted successively, for example by aspiration or/and irrigation, instead of having to extract a large volume piece completely all at once.

The at least one further incision may include at least one second incision that severs the tissue volume along one of the planes. For the purpose of generating such a second incision the control program may provide for a transmission to the eye of all the radiation pulses that impinge, in accordance with the meandering scan path, within the tissue volume bounded by the first incision. In this way, the entire area surrounded by the first incision can be cut in the plane in question. Outside this area it is preferred to blank all the radiation pulses. The second incision (or generally: each further incision serving for segmentation of the tissue volume) therefore preferentially only reaches as far as exactly the enveloping contour of the tissue volume to be removed, defined by the first incision. For this purpose the control program may be configured to bring about, in a plane for which the incision figure provides a second incision, a blanking of all those radiation pulses which are assigned to regions of the meandering scan path that lie outside the tissue volume. Within the scope of the invention, however, in principle it is not to be excluded to cause at least one further incision serving for segmentation of the tissue volume not to terminate directly at the first incision but rather to extend it beyond the first incision by a few photodisruptions. For example, adjacent to the line of intersection between the first incision and the plane in question, the first two, three or four radiation pulses may be allowed through to the eye.

Depending on the size of the tissue volume to be removed, and on the desired extent of the segmentation, it may be useful if the at least one further incision includes several second incisions that are superposed in each instance at a mutual distance of several planes.

Alternatively or additionally, the at least one further incision may include at least one third incision that extends transversely to the planes. By selective transmission of individual radiation pulses within the tissue volume across several planes, it is possible to generate incisions that sever the tissue volume, for example, perpendicularly to the planes. Such transversely extending incisions may, in particular, be useful when the tissue volume to be removed has a comparatively large extent in the x-y direction, so that segments with acceptably smaller x-y dimensions can be formed by generation of one or more third incisions. For example, by generation of a suitable number of second and third incisions it is conceivable to subdivide the tissue volume to be removed as a whole in the manner of cubes.

Advantageously, the control program is designed to sweep the planes with the radiation focus in the order of their superposed arrangement, and only after complete sweeping of the meandering scan path of one plane to move the radiation focus to a next plane.

According to a further aspect, the invention also makes available a process for laser-surgical treatment of the human eye, comprising:
  making available pulsed laser radiation with a radiation focus,
  generating, by means of the laser radiation, an incision figure in the cornea of an eye to be treated, the incision figure including a first incision that bounds a corneal tissue volume to be removed, and
  removing the tissue volume.

The generation of the first incision in this case requires a motion control of the radiation focus in the direction of propagation of the radiation (z-direction), the generating of the incision figure comprising:
  moving the radiation focus successively in a plurality of superposed planes in which a movement of the radiation focus is possible in each instance without motion control in the z-direction or direction of propagation of the radiation, whereby in each plane the radiation focus is moved along a meandering scan path that extends, at least in the region of its reversing-points, outside the tissue volume,
  in each plane, allowing to act on the eye at least such radiation pulses which serve for generating the first incision, and
  in at least a fraction of the planes, blanking of, in each instance, at least a fraction of those radiation pulses which are assigned to regions of the meandering scan path that are situated at a distance from the first incision.

The tissue volume to be removed may be situated completely within the cornea, i.e. the first incision may be a three-dimensional incision that is closed in itself. This situation may, for example, occur in the case of corneal lenticle extraction for the purpose of refractive correction of vision defects. Alternatively, the tissue volume to be removed may reach as far as the anterior surface of the cornea or the posterior surface of the cornea, for instance in the case of an epithelial corneal keratoplasty or an endothelial corneal keratoplasty. The first incision then has an edge situated on the anterior surface of the cornea or on the posterior surface of the cornea.

BRIEF DESCRIPTION OF THE DRAWINGS

The invention will be elucidated in more detail in the following on the basis of the appended schematic drawings. Represented are:
  FIG. 1 in schematic block representation, elements of a laser device for eye-surgical treatments according to an exemplary embodiment,
  FIG. 2a the generation of an intracorneal lenticle for a myopia correction according to an exemplary embodiment,
  FIG. 2b an exemplary machining pattern in a scan plane for the lenticle generation according to FIG. 2a,
  FIG. 2c an exemplary machining pattern in another scan plane for the lenticle generation according to FIG. 2a,
  FIG. 3 schematically, an intracorneal lenticle generation for a hyperopia correction,
  FIG. 4 schematically, an intracorneal lenticle generation for a myopia correction with comatic compensation,
  FIG. 5a schematically, an intracorneal lenticle generation for a myopia correction with segmentation of the lenticle according to an exemplary embodiment,
  FIG. 5b an exemplary machining pattern in a scan plane for the lenticle generation according to FIG. 5a, and
  FIG. 5c an exemplary machining pattern in another scan plane for the lenticle generation according to FIG. 5a.

DETAILED DESCRIPTION OF EXAMPLE EMBODIMENTS

Figure 1:
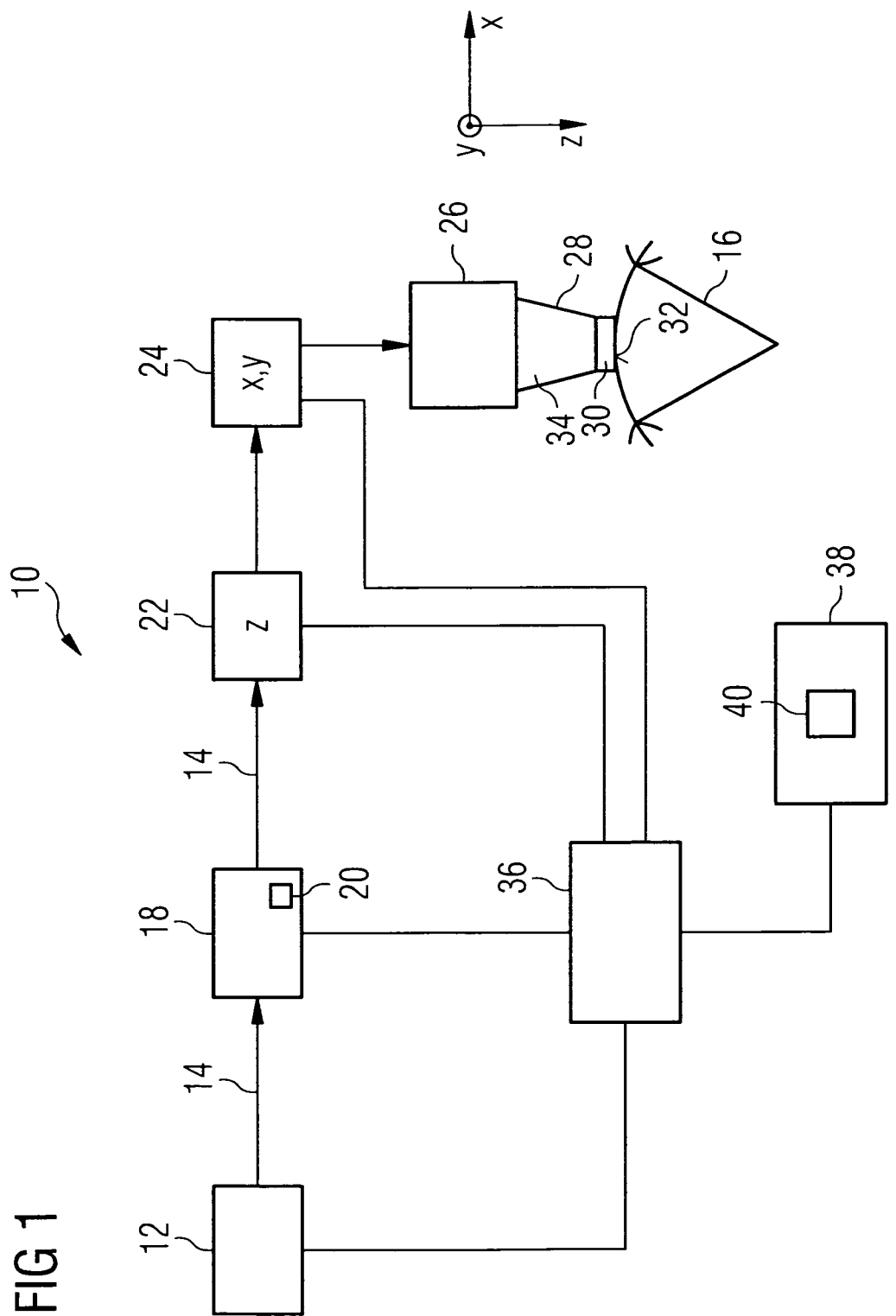

The laser device shown in FIG. 1—denoted generally therein by 10—includes a laser source 12 which makes available a pulsed laser beam 14 in which the pulse duration of the radiation pulses is suitable for use of the laser beam 14 for the purpose of generating incisions in the corneal tissue of an eye 16 of a patient to be treated. For example, the pulse duration of the radiation pulses of the laser beam 14 lies within the femtosecond or attosecond range. The laser beam 14 made available by the laser source 12 has a pulse repetition rate such as is desired for the application in question, i.e. the repetition rate of the radiation pulses emitted from the laser device 10 and directed onto the eye 16 corresponds to the repetition rate of the radiation pulses that are available at the output of the laser source 12, unless, in a manner depending on the machining profile predetermined for the eye 16, a fraction of the radiation pulses emitted from the laser source 12 are blanked by means of an optical switch 18 arranged in the beam path of the laser beam 14. Such blanked radiation pulses accordingly do not reach the eye 16.

In a manner not shown in any detail but known as such, the laser source 12 may include, for example, a laser oscillator (e.g. solid-state laser oscillator), a pre-amplifier, which increases the pulse power of the laser pulses emitted from the oscillator and simultaneously temporally stretches them, a subsequent pulse-picker, which selects individual pulses from the pre-amplified laser pulses of the oscillator, in order in this way to lower the repetition rate to a desired rate, a power amplifier, which amplifies the selected, still temporally stretched, pulses to the pulse energy needed for the application, and a pulse compressor, which temporally compresses the pulses output from the power amplifier to the pulse duration desired for the application.

The optical switch 18, which may also be designated as a pulse modulator, may, for example, be designed as an acousto-optical modulator or as an electro-optical modulator. Generally, the optical switch 18 may contain optically active elements that enable a rapid blanking of individual laser pulses. The optical switch 18 may, for example, contain a beam trap indicated schematically at 20, which serves to absorb radiation pulses to be blanked, which are not to reach the eye 16. The optical switch 18 can deflect such radiation pulses to be blanked out of the normal beam path of the radiation pulses of the laser beam 14 and direct them onto the beam trap 20.

In the beam path of the laser beam 14 further optical components are arranged which, in the exemplary case shown, include a z-scanner 22, an x-y scanner 24 and also a focusing objective 26. The focusing objective 26 serves for focusing the laser beam 14 onto a desired machining location on or in the eye 16, in particular in the cornea of the same. The z-scanner 22 serves for longitudinal control of the location of the focal point of the laser beam 14; the x-y scanner 24 serves, on the other hand, for transverse control of the location of the focal point. 'Longitudinal' relates in this connection to the direction of beam propagation; this is designated in conventional notation as the z-direction. 'Transverse', on the other hand, designates a direction transverse to the direction of propagation of the laser beam 14; according to conventional notation the transverse plane is designated as the x-y plane. A coordinate frame that represents the x-y-z directions in the region of the eye 16 has been drawn in FIG. 1 for the purpose of illustration.

For the purpose of transverse deflection of the laser beam 14, the x-y scanner 24 may, for example, include a pair of galvanometrically actuated scanner mirrors that are capable of tilting about mutually perpendicular axes. On the other hand, the z-scanner 22 may, for example, contain a longitudinally adjustable lens or a lens of variable refractive power or a deformable mirror, with which the divergence of the laser beam 14 and consequently the z-position of the beam focus can be influenced. For example, such an adjustable lens or mirror may be contained in a beam expander which is not represented in any detail and which expands the laser beam 14 emitted from the laser source 12. The beam expander may, for example, be configured as a Galilean telescope.

The focusing objective 26 is preferably an f-theta objective and is preferentially detachably coupled on its beam-exit side with a patient adapter 28 which constitutes an abutment interface for the cornea of the eye 16. For this purpose the patient adapter 28 exhibits a contact element 30 that is transparent to the laser radiation and that on its underside facing towards the eye exhibits an abutment surface 32 for the cornea. In the exemplary case shown, the abutment surface 32 is realised as a plane surface and serves for levelling the cornea, by the contact element 30 being pressed against the eye 16 with appropriate pressure or by the cornea being aspirated onto the abutment surface 32 by underpressure. The contact element 30, which in the case of plane-parallel design is ordinarily designated as the applanation plate, is fitted to the narrower end of a conically widening carrier sleeve 34. The connection between the contact element 30 and the carrier sleeve 34 may be permanent, for example by virtue of adhesion bonding, or it may be detachable, for instance by virtue of a screw coupling. In a manner not represented in any detail, the carrier sleeve 34 has at its wider sleeve end, which in the drawing is the upper end, suitable coupling structures for coupling to the focusing objective 26.

It will be understood that the order of the optical switch 18, the z-scanner 22, the x-y scanner 24 and the focusing objective 26 does not have to be as represented in FIG. 1. For example, the optical switch 18 may readily have been arranged in the beam path downstream of the z-scanner 22. The order of these components shown in FIG. 1 is, to this extent, in no way to be understood as limiting.

The laser source 12, the optical switch 18 and also the two scanners 22, 24 (which, if desired, may also have been combined in a single structural unit) are controlled by a control computer 36 which operates in accordance with a control program 40 stored in a memory 38. The control program 40 contains instructions (program code) that bring about, upon execution by the control computer 36, such a control of the location of the beam focus of the laser beam 14 that in the cornea of the eye 16 bearing against the contact element 30 an incision figure arises that completely severs from the surrounding corneal tissue a corneal tissue volume to be removed within the scope of a corneal lenticle extraction or a corneal keratoplasty. If desired, this incision figure may additionally bring about a segmentation of this tissue volume into a plurality of volume segments individually separated from one another.

For a first exemplary embodiment of a corneal lenticle extraction, reference will now be made to FIG. 2a. The cornea of the eye to be treated, which is bearing against the abutment surface 32 of the contact element 30, is indicated therein schematically at 42; its anterior surface is denoted by 44. Drawn, in addition, is an intrastromal lenticle 46 that is suitable for a myopia correction and that is separated from the surrounding corneal tissue all round by a three-dimensional incision 48, closed in itself, and is capable of being extracted from the cornea 42 through an access incision which is not represented in any detail. After removal of the lenticle 46, the anterior corneal region located upstream of the cavity that has then arisen drops down as far as the (posterior) floor of this cavity, and/or a raising of the posterior floor occurs towards the anterior side of the cavity. This is accompanied by a reshaping of the anterior surface 44 of the cornea, as a result of which, correspondingly, a myopia of the eye 16 to be treated can be eliminated or at least reduced.

For the generation of the incision 48, which is a first incision in the sense of the invention, the beam focus of the laser beam 14 of the laser device 10 shown in FIG. 1 is controlled in such a manner that it passes successively through a plurality of planes (scan planes) and, in each of these planes, scans a predetermined scan pattern that is independent of the concrete shape of the tissue volume to be removed (here: lenticle 46). Wherever the scan pattern in the plane in question touches or intersects the surface of the incision 48 to be generated, laser pulses are allowed through by the optical switch 18, so that a photodisruption is brought about at these points. In the remaining regions of the scan pattern the laser pulses are blocked, i.e. blanked, by the optical switch 18, so that in these regions no laser pulses reach the eye and accordingly no photodisruption is brought about. After the scan pattern has been completely scanned in one plane, the beam focus is moved to the next, adjacent plane, and the procedure is repeated there. In this way, all the planes are passed through successively by the beam focus. After total passage through all the planes, the incision 48 has been generated completely and the lenticle 46 has been cut free. Expediently the planes are passed through, one after the other, in the direction from posterior to anterior, i.e. beginning at the most low-lying plane and going as far as the plane situated nearest to the anterior surface 44 of the cornea. In this manner, shading effects can be avoided that may arise if the laser beam is focused to more low-lying tissue regions through a plane in which an incision has already been made.

In FIG. 2a some of the planes are indicated at $50_1$ to $50_6$ for the purpose of illustration only. A characteristic feature of the scan planes is that in each plane the beam focus can be moved solely by appropriate control of the x-y scanner 24; but a control of the z-scanner 22 is not required for a focus movement in the plane in question. In the case where use is made of an f-theta objective for the focusing optics 26—that is to say, plane-field optics—the planes in which the beam focus can be moved without z-control are planar x-y planes. If, however, plane-field optics are not employed for focusing the laser beam 14, it is conceivable that the planes in which the beam focus is moved, in each instance in accordance with the predetermined scan pattern, are curved.

Drawn in FIG. 2a, furthermore, are a plurality of filled-in black circles 52 which each illustrate a photodisruption. These photodisruptions 52 are situated at the points where the scan planes $50_1 \ldots 50_6$ intersect the (intended) incision 48. The spacing of consecutive scan planes is chosen in such a manner that by juxtaposition of photodisruptions in various planes an incision passing across several scan planes can be generated. On the assumption that the size of a photodisruption 52 corresponds, at least in rough approximation, to the waist diameter (focus diameter) of the laser beam 14, the mutual spacing of consecutive scan planes is, for example, of the order of magnitude of a few μm, for example between 1 μm and 5 μm. Given a maximal thickness of the lenticle 46 of, for example, about 100 μm (this is a not atypical value in the case of a myopia correction by intrastromal lenticle extraction), at least about 20 scan planes then have to be provided, in which the beam focus is moved in each instance along the predetermined scan pattern.

Figure 2B:
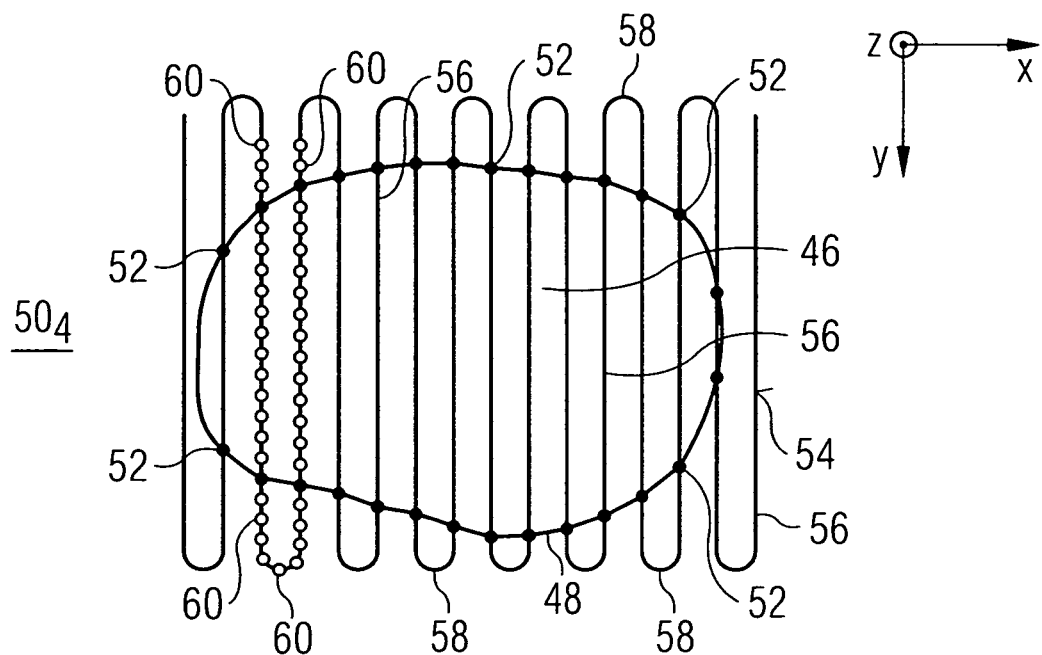
Figure 2C:
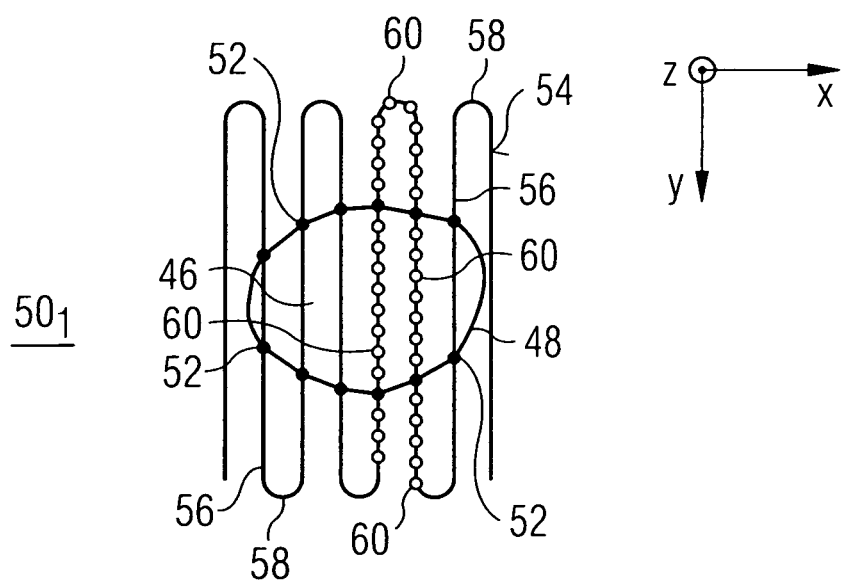

With a view to more detailed elucidation of an exemplary scan pattern, reference will now be made to FIGS. 2b and 2c, in which FIG. 2b is a z-direction top view of a scan plane in which the lenticle 46 has larger diameter and FIG. 2c is a z-direction top view of a scan plane in which the lenticle 46 has smaller diameter. In exemplary manner in this respect, the scan planes $50_4$ for FIG. 2b and $50_1$ for FIG. 2c are indicated.

The scan pattern that is used in the exemplary embodiment shown is a meandering scan path 54 which is composed of a plurality of rectilinear path portions 56 extending next to one another in parallel, which in the region of their ends are connected by reversing-portions 58 so as to form a tortuous path. The reversing-portions 58 may be curved in the manner of an arc or may be configured in angular manner. In a manner similar to the mutual spacing of the scan planes, the spacing of rectilinear path portions 56 situated next to one another is of the order of magnitude of the focus diameter, so that in the scan plane in question a one or two-dimensional incision (line or area) passing through across these path portions 56 can be generated by placing photodisruptions in adjacent path portions 56. It will be understood that the graphical representation of the meandering scan path 56 in FIGS. 2b and 2c does not reflect the real size ratios proportionally. It is expressly a question of schematic representations that serve merely for illustration.

The reversing-portions 58 of the meandering scan path 54 lie outside the lenticle 46 to be generated—in other words, outside the tissue volume bounded by the incision 48. Preferentially, all the photodisruptions are generated only in such regions of the meandering scan path 54 which pertain to the rectilinear path portions 56. Since, on the assumption of an invariable pulse repetition rate of the radiation pulses emitted from the laser source 14, the local spacing of consecutive focal positions is constant, at least on the rectilinear path portions 56, in this way an undesirable heating of tissue or separation of tissue by virtue of a local increase in density of photodisruptions can be avoided.

As in FIG. 2a, in FIGS. 2b and 2c the photodisruptions 52 are each indicated by filled-in black circles. Circles 60 which are not filled in illustrate, on the other hand, focal positions along the meandering scan path 54 at which the radiation pulses are blanked. These positions may also be designated as blanking positions. For reasons of clarity of layout, only a small fraction of the blanking positions 60 have been indicated graphically. It is readily comprehensible that for the purpose of generating the incision 48 in each scan plane a considerably larger number of radiation pulses are blanked than are allowed though.

According to the representation in FIGS. 2b and 2c, the meandering scan path 54 is identical in all scan planes, i.e. in particular the length of the rectilinear path portions 54 across the scan planes is the same. This does not have to be the case. Depending on the diameter of the lenticle 46 in the scan plane in question, it is conceivable to make the length of the rectilinear path portions 56 shorter or longer or/and to vary the number of rectilinear path portions 56, in order in this way to configure the scan pattern to be wider or less wide. However, the mutual spacing of consecutive rectilinear path portions 56 remains the same in each scan plane.

In the following Figures further exemplary embodiments are shown in which identical or identically-acting elements are denoted by the same reference symbols as in FIGS. 2a to 2c but supplemented by a lower-case letter. Unless stated otherwise below, for the purpose of elucidating these identical or identically-acting elements reference is made to the remarks above.

FIG. 3 shows an example of an intrastromal lenticle 46a that is suitable for a hyperopia correction. In contrast to FIG. 2a, where the lenticle 46 is approximately discus-shaped and has its greatest thickness roughly in the middle, the lenticle 46a according to FIG. 3 displays a striking reduction in thickness in its middle, this reduction in thickness being brought about by an appropriately concave configuration of the posterior portion of incision 48a. The anterior portion of the incision 48a is, as in the exemplary embodiment shown in FIG. 2a, configured to be convex. Alternative lenticle shapes are, of course, possible.

The incision 48a is also generated in the manner described previously for the lenticle 46 shown in FIG. 2a, by the radiation focus being moved in a plurality of superposed scan planes $50a_1 \ldots 50a_i$ which are each capable of being scanned solely by x-y control, in each instance along a predetermined scan path that is independent of the lenticle shape, in particular along a meandering scan path, and radiation pulses are allowed through to the eye only where the incision 48a (to be generated) intersects the scan path in the plane in question. Otherwise the radiation pulses are blanked.

Figure 4:
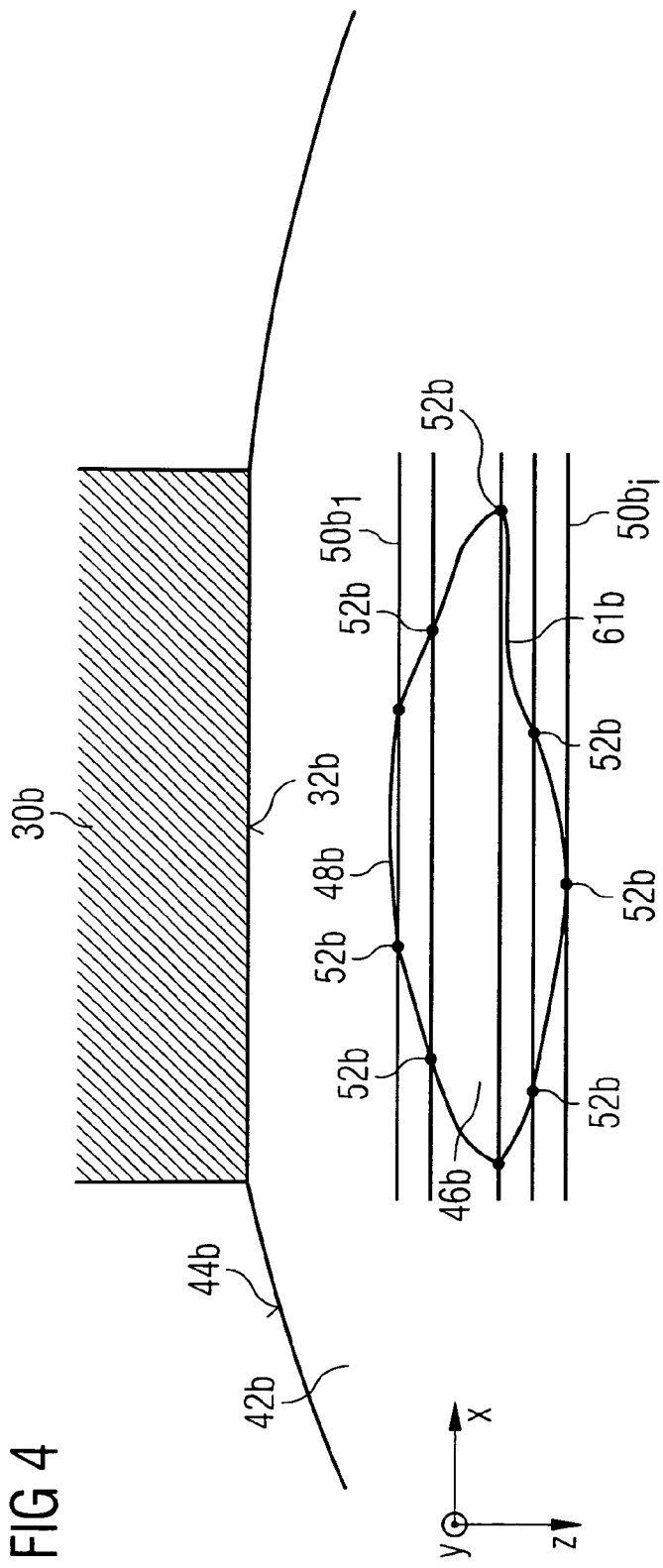

As a further example, FIG. 4 shows an intrastromal lenticle 46b to be extracted which is bounded by an incision 48b closed in itself and which is suitable for the correction of a myopia with a comatic component. In addition, some scan planes $50b_1 \ldots 50b_i$ and also some photodisruptions 52b are indicated which lie in these scan planes. The lenticle 46b is configured similarly to the lenticle 46 shown in FIG. 2a but on its (posterior) underside has an eccentric indentation 612b for taking the comatic component into account.

It will be readily comprehended that with the described procedure of scanning predetermined scan paths in succession in a plurality of superposed scan planes three-dimensional incisions that are arbitrary in themselves, and correspondingly tissue volumes in the cornea that are arbitrarily shaped in themselves, can be cut free. In this connection, the tissue volume in question may lie totally deep within the corneal tissue, as in the exemplary cases shown in FIGS. 2a to 4. Alternatively, the tissue volume to be cut free may be bounded by a part of the anterior surface of the cornea or by a part of the posterior surface of the cornea, as in the case of an epithelial or endothelial corneal keratoplasty.

In the previous exemplary cases it was assumed that photodisruptions are placed merely at the periphery of the tissue volume to be extracted—that is to say, on the surface of incision 48, 48a or 48b. In other words, it was assumed that the tissue volume to be extracted is to be surgically removed as an individual, continuous piece of tissue. This may be inappropriate, particularly in the case of comparatively large tissue volumes. One variant therefore provides that, when passing through the various scan planes, photodisruptions are placed not only at the periphery of the tissue volume to be cut free but also within this tissue volume, in order in this way to obtain a segmentation by which the tissue volume is subdivided into several partial volumes. With a view to illustrating this variant, reference will now be made in exemplary manner to FIGS. 5a, 5b and 5c.

The representations in these Figures are based on the purely exemplary assumption that the tissue volume to be removed as a whole is to be suitable for a myopia correction. Even though, according to the exemplary embodiment shown in FIGS. 5a to 5c, this tissue volume to be removed as a whole is no longer present as an integral lenticle but has been subdivided into a plurality of partial volumes each capable of being extracted separately, the entire tissue volume is nevertheless denoted by 46c. The incision surrounding this tissue volume 46c is denoted by 48c. Drawn in FIG. 5a, in addition, are some exemplary scan planes $50c_1$ to $50c_7$. In each of these scan planes (generally, in all scan planes) the beam focus is moved along the same scan pattern, which is preferably also identical in terms of size, here along a meandering scan path.

In the exemplary case shown in FIG. 5a the tissue volume 46c is segmented in the manner of cubes or right parallelepipeds, for which purpose in a fraction of the scan planes an incision severing the tissue volume 46c completely is generated. In the exemplary case shown in FIG. 5a, the scan planes $50c_2$ and $50c_4$ are such planes in which the tissue volume 46c is transected completely. The incisions generated in these planes are, in each instance, a second incision in the sense of the invention; according to FIG. 5b (which shows the plane $50c_2$ in exemplary manner) they are generated by all radiation pulses lying within the tissue volume 46c—that is to say, within the boundary formed by the incision 48c—in the scan plane in question being allowed through. As a result, in this way in the scan plane in question an incision is generated that reaches at least as far as and preferably not further than the incision 48c. This incision is denoted in FIG. 5b by 62c. Those radiation pulses which in the scan plane in question lie outside the incision 48c are preferably blanked completely. Particularly in the reversing-regions 58c of the meandering scan path 54c of the scan plane in question, no radiation pulses get through to the eye.

Depending, for example, on the thickness of the tissue volume 46c, it may suffice to generate an incision 62c in a single scan plane, or it may be necessary to generate such an incision 62c in each instance in several scan planes. In the latter case, between a pair of scan planes in which an incision 62c is generated in each instance there are situated, in each instance, several scan planes in which no such incision 62c is generated. For example, two adjacent incisions 62c may be spaced from one another by the order of magnitude of ten or a hundred scan planes.

In the remaining scan planes—that is to say, where no incision 62c is generated—in the exemplary embodiment shown in FIGS. 5a to 5c such a pass control of the radiation pulses is effected that within the tissue volume 46c in each instance a fraction of the radiation pulses are allowed through, specifically in such a way that in the scan planes in question in each instance one or more incision lines (i.e. a string of photodisruptions) arise. Such incision lines are indicated in FIG. 5c (which shows the plane $50c_5$ in exemplary manner) at 64c. In principle, incision lines 64c can be generated in arbitrary number and with arbitrary shape. In the exemplary case shown in FIG. 5c, a plurality of incision lines 64c are provided overall which together form a grid. If such a grid of incision lines 64c is generated in several superposed scan planes, a segmentation, e.g. in the manner of cubes or right parallelepipeds, of the tissue situated within the volume 46c can be obtained. The incisions arising in this case, which are formed by the incision lines 64c, are, in each instance, a third incision in the sense of the invention; these third incisions are denoted in FIG. 5a by 66c. They may be oriented parallel to the z-direction, but if desired also obliquely thereto.

In FIG. 5a, which serves solely for illustrative purposes, the scan planes $50c_1$, $50c_3$, $50c_5$ and $50c_7$ are such scan planes in which linear incisions 64c are generated which result in the formation of incisions 66c.

The partial volumes that are capable of being generated by such segmentation of the tissue volume 46 (segmentation by incisions 62c or/and 66c) have in the x-y plane, for example, a maximal edge length from 0.1 mm to 1 mm, in which connection it will be understood that these numerical values are under no circumstances limiting. Similar numerical values may, for example, also be assumed for the segment size in the z-direction.

Instead of a cross-grating—such as is represented in FIG. 5c and formed from a plurality of incision lines 64c intersecting one another, for example, at right angles—it is equally possible to generate in individual scan planes in each instance a line grating which is formed merely from incision lines 64c extending next to one another at a distance and not intersecting one another.

The invention enables a quasi-continuous fragmentation of a desired corneal lenticle by close juxtaposition of a plurality of photodisruptions (in each instance generated by a laser-induced optical breakthrough) in the lenticle volume and by appropriately small spacing of the incisions passing through the lenticle (e.g. incisions 62c, 66c), so that the fragmented corneal tissue, which may have three-dimensional shaping that in itself is arbitrary, can be removed, for example drawn off by suction, through an extremely small incision in the stroma.

Such a quasi-continuous photodisruptive fragmentation of the lenticle can be obtained by suitable spacings of the focal positions and incision planes within the desired lenticle volume. By keying and blanking the laser pulses provided for in the control program for the purpose of lenticle generation, to a large extent arbitrarily selectable incision contours in the cornea can be generated. The switching-on of the laser pulses may relate, according to one configuration, merely to those laser pulses provided for in the control program which define the volume contour of the lenticle (cf. for example the embodiments according to FIGS. 2 to 4). Alternatively, the switching-on may additionally relate to such laser pulses which are provided for in the control program for regions within the volume contour of the lenticle or/and outside the same (cf. for example the embodiment according to FIGS. 5a to 5c).

The invention claimed is:

1. Device for surgery on the human eye, the device comprising:
    a laser apparatus for providing pulsed focused laser radiation, the laser apparatus being controlled by a control program in such a manner that by application of the laser radiation it generates an incision figure in the cornea of an eye to be treated, the incision figure including a first incision that defines a 3-dimensional corneal tissue volume to be removed,
    wherein the generation of the first incision requires a motion control of the radiation focus in the direction of propagation of the radiation,
    wherein the control program is designed in such a manner that for the generation of the incision figure the radiation focus is moved successively in a plurality of superposed planes in which a movement of the radiation focus is possible in each instance without motion control in the direction of propagation of the radiation,
    wherein for each plane the control program provides for a meandering scan path of the radiation focus that, at least in a region of its reversing-points of the meandering scan path, extends outside the tissue volume,
    wherein the control program allows through to the eye, in each plane, at least such radiation pulses which serve for generating the first incision, wherein the control program blanks, in at least a partial number of the planes, those radiation pulses which are assigned to regions of the meandering scan path that are situated at a distance from the first incision.

2. Device according to claim 1, wherein the control program allows through to the eye in at least a partial number of the planes, only such radiation pulses which serve for generating the first incision.

3. Device according to claim 1, wherein the incision figure includes at least one further incision that subdivides the tissue volume bounded by the first incision into partial volumes that are separate from one another, wherein the control program allows through to the eye, in the planes, at least such radiation pulses which serve for generating the at least one further incision.

4. Device according to claim 3, wherein the at least one further incision includes at least one second incision that severs the tissue volume along one of the planes.

5. Device according to claim 4, wherein the control program, in a plane for which the incision figure provides a second incision, blanks all those radiation pulses which are assigned to regions of the meandering scan path that lie outside the tissue volume.

6. Device according to claim 4, wherein the at least one further incision includes several second incisions that are superposed in each instance at a mutual distance of several planes.

7. Device according to claim 3, wherein the at least one further incision includes at least one third incision that extends transversely to the planes.

8. Device according to claim 1, wherein the control program sweeps the planes with the radiation focus in the order of their superposed arrangement, and only after complete sweeping of the meandering scan path of one plane to move the radiation focus to a next plane.

* * * * *